(12) United States Patent
Muscat et al.

(10) Patent No.: US 6,347,930 B1
(45) Date of Patent: Feb. 19, 2002

(54) DEVICE AND METHOD FOR MANUFACTURING A SEGMENTED TUBULAR CAPSULE CONTAINING A BIOLOGICALLY ACTIVE MEDIUM

(75) Inventors: Eric Muscat, Villeurbanne; Claude Brun, Lyons, both of (FR)

(73) Assignee: Hospal R & D Int., Meyzieu (FR)

( * ) Notice: Subject to any disclaimer, the term of this patent is extended or adjusted under 35 U.S.C. 154(b) by 0 days.

(21) Appl. No.: 09/643,710

(22) Filed: Aug. 23, 2000

Related U.S. Application Data

(62) Division of application No. 09/254,593, filed as application No. PCT/FR97/01609 on Sep. 11, 1997.

(51) Int. Cl.[7] .............................. B28B 1/54; B28B 5/00; B28B 21/52; B28B 21/00; B28B 17/00
(52) U.S. Cl. ............................ 425/5; 425/71; 425/322; 425/391; 425/194; 264/4
(58) Field of Search ................................ 435/182, 180, 435/288; 424/400, 423, 424; 425/382, 5, 71, 322, 391, 194; 264/4

(56) References Cited

U.S. PATENT DOCUMENTS 5,158,881 A * 10/1992 Aebischer et al. .......... 435/182

FOREIGN PATENT DOCUMENTS

| EP | 0 200 224 A2 | 11/1986 |
| WO | WO 91/10425 | 7/1991 |

OTHER PUBLICATIONS

J. Honiger et al., "Permeability and Biocompatibility and Biocompatibility of a New Hydrogel Used for Encapsulation of Hepatocyptes," Biomaterials 16:753–759 (1995).

* cited by examiner

Primary Examiner—Thurman K. Page
Assistant Examiner—Blessing Fubara
(74) Attorney, Agent, or Firm—Finnegan, Henderson, Farabow, Garrett & Dunner, L.L.P.

(57) ABSTRACT

A device for manufacturing tubular fibre includes an extrusion head through which a polymer and a biologically active material flow. The biologically active material is encapsulated within compartments formed in the fibre. Partial solidification is caused by structure, such as a coagulation bath, adjacent the extrusion head. This prevents breakage of the fibre as it leaves the head.

14 Claims, 3 Drawing Sheets

DEVICE AND METHOD FOR MANUFACTURING A SEGMENTED TUBULAR CAPSULE CONTAINING A BIOLOGICALLY ACTIVE MEDIUM

This is a division of application Ser. No. 09/254.593, filed Apr. 16, 1999, claiming priority based on PCT/FR97/01609, filed Sep. 11, 1997, and French 96/11346, filed Sep. 12, 1996, which are incorporated herein by reference.

BACKGROUND OF THE INVENTION

Field of the Invention

The present invention relates to the manufacture of a capsule containing a biologically active medium, intended to be implanted in a living organism for therapeutic purposes. In the conventional way, a capsule of this type consists of a core comprising a biologically active medium, which is surrounded by a semipermeable casing. The role of the casing is to isolate the biologically active medium from the tissues of the receiving organism while at the same time allowing substances via which the implanted capsule fulfils its functions to pass through the casing. By way of example, when the biologically active medium is a suspension of cells, the semipermeable casing must act as a barrier to immune reactions, must allow nutrients to diffuse towards the core of the capsule and must allow the substance of therapeutic benefit secreted by the cells (insulin, for example, when the cells are islets of Langerhans) to diffuse towards the organism.

From the point of view of the efficiency of the exchanges across the membrane, it would seem that spherical capsules are preferred over tubular capsules. However, spherical capsules have the drawback of being difficult to locate when implanted, which means that at the present time it would not be possible to implant them in a human body from which the implants have always to be able to be extracted for reasons of biological safety.

Recent research has therefore been mainly centred on manufacturing tubular capsules, which allow the shaping of implants that are long enough that they can be easily found. In particular, it has been discovered that it is preferable to segment the tubular capsules, that is to say to form therein compartments which are isolated from one another, so that if part of an implanted capsule is damaged, it is possible to separate it from the implant and extract it from the receiving organism.

U.S. Pat. No. 5,158,881 describes a method of manufacturing a segmented tubular capsule, comprising the steps of:

coextruding a polymer solution intended to form the casing of the capsule and a biologically active medium by simultaneously injecting the polymer solution and the biologically active medium through a die, and interrupting the injection of the biologically active medium at determined points in time to form in the fibre successive compartments full of the biologically active medium and separated by a solid partition section consisting only of the polymer solution.

This method does not yield the desired results when the polymer solution is liquid because, when the injection of biologically active medium is interrupted, a drop of polymer solution forms under the die, deforms and breaks under the effect of the weight of the fibre already formed which hangs from the die.

The object of the invention is to improve the above-described method in such a way as to make it possible to manufacture a segmented tubular capsule from a liquid polymer solution. Another object of the invention is to shape a tubular capsule into a shape that can be directly implanted.

To achieve this objective, there is provided, according to the invention, a method of manufacturing a tubular capsule comprising a wall delimiting internal compartments that are isolated from one another, the wall being made from a solution of at least one polymer and the compartments being full of a biologically active medium, the method comprising:

coextruding the solution of at least one polymer and the biologically active medium by simultaneously injecting the polymer solution and the biologically active medium through a die of determined dimensions, interrupting the injection of the biologically active medium at determined points in time to form in the fibre successive compartments full of the biologically active medium and separated by a partition section made of the polymer solution:

causing partial early solidification of the fibre as it leaves the die to a sufficient extent to prevent the fibre from breaking at the partition sections.

As a preference, partial early solidification of the fibre may include:

immersing the fibre in a coagulation liquid as it leaves the die so as to initiate early coagulation of the polymer solution around the outside of the fibre; and simultaneously driving the fibre through the coagulation liquid along a determined path.

This method may have at least two major benefits. On the one hand, it makes it possible to envisage industrial-scale or semi-industrial-scale implant production. On the other hand, bringing the fibre leaving the die into early contact with the coagulation liquid allows some of the solvent used to prepare the polymer solution to be extracted, which is something that is particularly desirable to be extracted, which is something that the particularly desirable when the biologically active medium contains living cells which may be adversely affected by the solvents commonly used.

According to one feature of the invention, the method further comprises, at the same time as partially solidifying the fibre, exerting a determined tensile force on the fibre so as to give it at least one geometric characteristic that is independent of the dimensions of the die.

By virtue of this arrangement, it is possible to extrude low viscosity polymer solutions.

According to another feature of the invention, the method furthermore comprises giving the fibre a permanent shape. For example, the fibre is wound onto a cylindrical mandrel in such a way as to adopt the shape of a spiral, the pitch of which is chosen to be such that each section of the fibre comprising a whole number of compartments corresponding to an implantable capsule occupies a determined length of mandrel.

By virtue of this arrangement, the dimensions of the implantable capsule can be adjusted to suit the size of the receiving organism. It has been found that the spiral-wound shape was particularly well-suited to implants in that it gave them mechanical robustness, in that it made them easier to handle and in that it made them easier to implant in an organism.

Another subject of the invention is a device for manufacturing a tubular fibre comprising a wall delimiting internal compartments isolated from one another and full of a biologically active medium, comprising:

extrusion means of determined dimensions for coextruding a solution of at least one polymer and the biologically active medium in such a way as to obtain a tubular fibre having a wall made from the polymer solution and filled with the biologically active medium;

means for supplying the extrusion means with the polymer solution and with the biologically active medium;

means for controlling the simultaneous supply of the extrusion means with polymer solution and with biologically active medium and for interrupting the supply of biologically active medium at determined points in time so as to form within the fibre successive compartments filled with the biologically active medium and separated by a solid partition section consisting only of the polymer solution;

the device being characterized in that it comprises:

means for causing partial solidification of the fibre as it leaves the extrusion means, this solidification being enough to prevent the fibre from breaking at the partition sections.

As a preference, the solidification means comprise:

a bath for a coagulation liquid placed under the extrusion means at a chosen distance so that a fibre flowing out from the die at a given output rate begins to coagulate early from the outside and does not break; and means for driving the fibre through the coagulation liquid along a determined path.

According to one feature of the invention, the device further comprises means for exerting a determined tensile force on the fibre so as to give it at least one geometric characteristic that is independent of the dimensions of the extrusion means.

In one embodiment of the invention, the driving means and the means for exerting a tensile force comprise a tube passing through the bottom of the coagulation bath and having an upper end inside the bath and a lower end outside the bath, this tube being arranged substantially vertically and its upper end lying below the surface of the coagulation liquid when the bath is filled to a determined operating level.

This embodiment is particularly advantageous because it allows several functions to be fulfilled using very simple and inexpensive technical means. Furthermore, it is easy to regulate and allows very low tensile forces to be exerted on the fibre, if appropriate.

According to one feature of the invention, the device further comprises means for giving the fibre a determined shape. For example, the shape chosen is a spiral and the means for giving the fibre this shape comprise:

a mandrel made up of disassemble portions;

means for rotating the mandrel;

a guiding device for moving the fibre with a back and forth movement parallel to the mandrel.

Advantageously, in operation, the rotational speed of the mandrel and the speed of the back and forth movement of the guiding device are chosen so that the portion of fibre wound in a spiral onto the length of a portion of mandrel corresponds approximately to a determined whole number of internal compartments of the fibre.

By virtue of this arrangement, it is possible to limit the handling of the shaped fibre as far as possible: all that is required is to ensure that the length of fibre needed to form an implantable capsule is wound onto each mandrel portion. When the fibre is wound along the entire length of the mandrel, the fibre is cut at the junction between two contiguous mandrel portions and the mandrel portions are separated and can act as supports for the implantable capsules during despatch and storage.

Other features and advantages of the invention will become clear from reading the description which follows.

BRIEF DESCRIPTION OF SEVERAL VIEWS OF THE DRAWINGS

Reference will be made to the appended drawings, in which.

DESCRIPTION OF PREFERRED EMBODIMENTS

Figure 1:
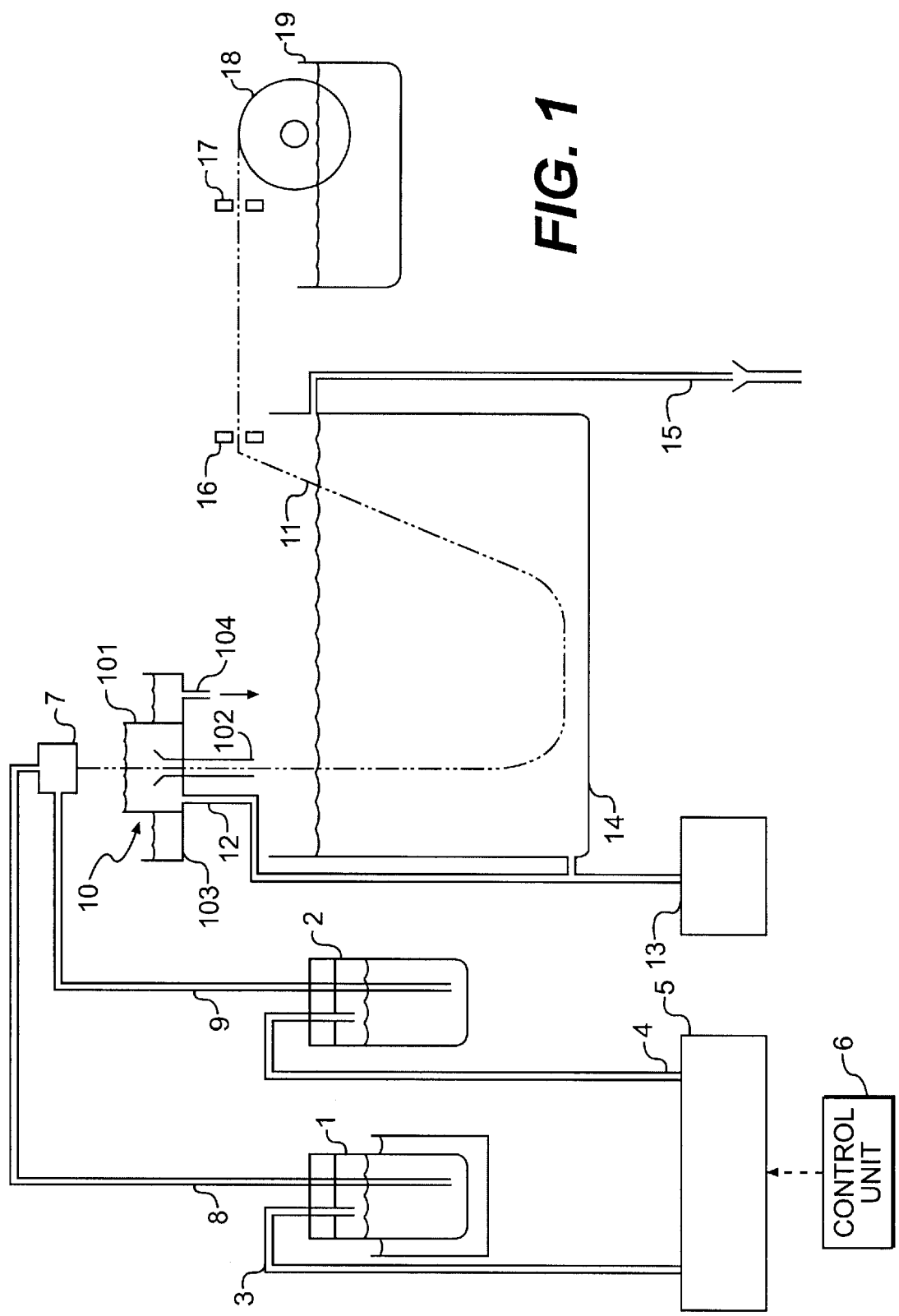
FIG. 1 depicts, diagrammatically, a plan view of a first part of a device for manufacturing a segmented tubular capsule according to the invention.

The device of FIG. 1 comprises a first reservoir 1 for containing a biologically active medium, in liquid form, such as a suspension of cells. This reservoir is placed in a temperature control chamber allowing the contents of the reservoir 1 to be kept at constant temperature. There is a second reservoir 2 for containing a polymer solution. The two reservoirs 1 and 2 are hermetically sealed and are connected by pipes 3, 4 to a gas-pressure regulating system 5 that allows a constant pressure to be set and maintained in each reservoir. The pressure-regulating system 5 is connected to a control unit 6 which controls the pressure regulation in each reservoir on the basis of datum values communicated beforehand to the control unit 6 by an operator, using a keyboard (not depicted).

The reservoirs 1 and 2 and the gas-pressure regulating system 5 constitute the means of supplying extrusion means 7 which have two concentric tubular nozzles, the inner nozzle 71 being connected by pipe 8 to the reservoir 1, and the outer nozzle 72 being connected by a pipe 9 to the reservoir 3.

Figure 2:
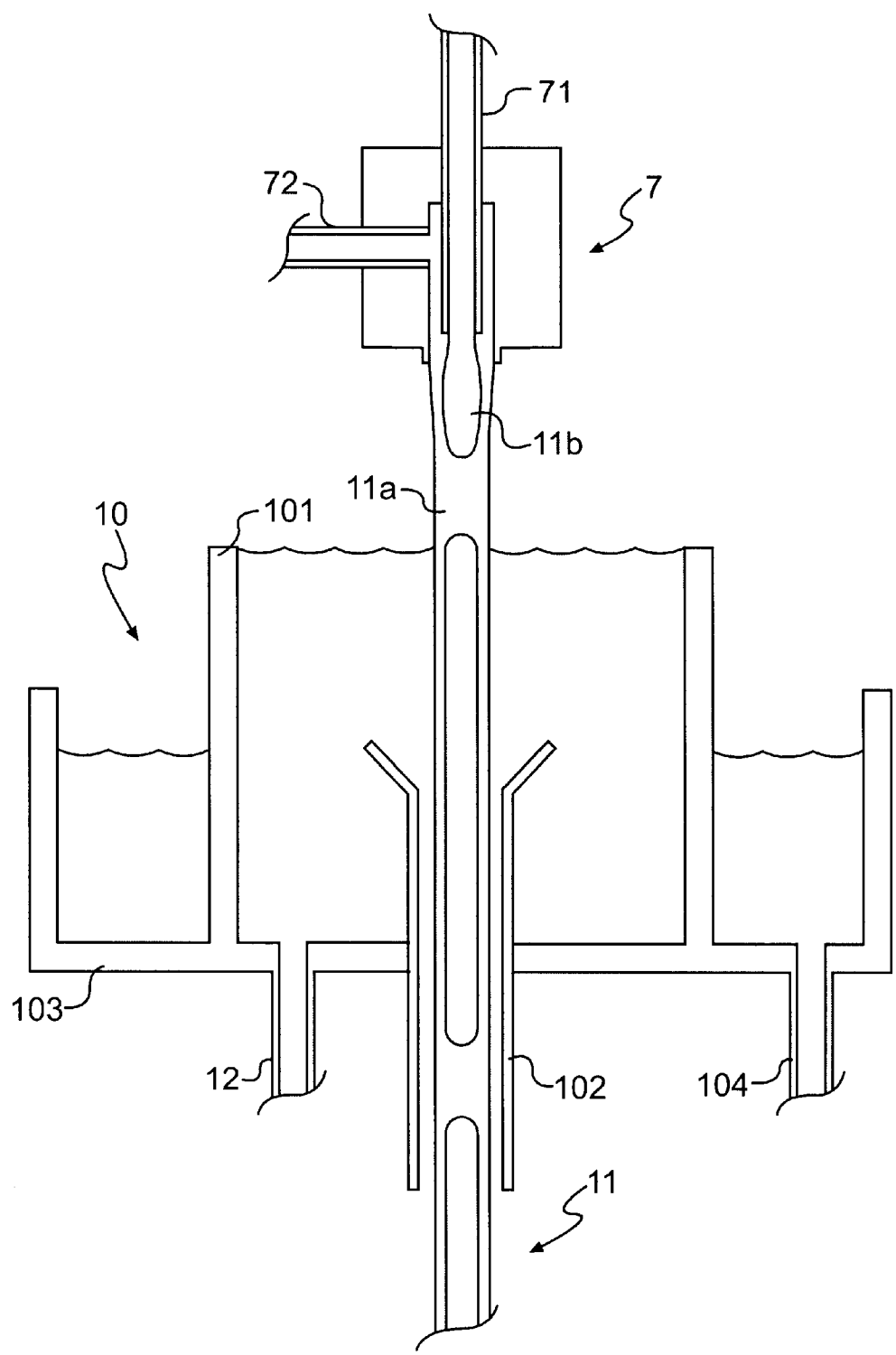
FIG. 2 depicts, diagrammatically, the extrusion and solidification means of the device according to the invention.

In accordance with the invention, means 10 for causing early solidification of a tubular fibre 11 exiting the extrusion means are arranged vertically in line with the concentric nozzles 71, 72. As can be seen in greater detail in FIG. 2, these early solidification means comprise a coagulation bath 101 with a bottom pierced by a hole for the passage of a tube 102, flared at its top, the central longitudinal axis of which is essentially aligned with the central longitudinal axis of the nozzles 71, 72. As a result of this layout, the tube 102 has a top end inside the coagulation bath 101 and a bottom end outside this bath. The tube 102 is mounted so that it can be slid in a vertical direction, so that the height of water between the top end of the tube 102 and a reference water level in the coagulation bath 102 can be set accurately.

The choice of length of the tube 102, of its inside diameter, and of the height of water between the reference level and the top end of the tube allows the action exerted on the fibre, simple driving or pulling, to be regulated accurately. For the same head of water, and for a tube of the same inside diameter, the longer the tube, the lower the tension. For the same head of water, and for a tube of the same length, the smaller the inside diameter of the tube, the lower the tension. For the same length of tube and the same inside diameter, the lower the head of water, the lower the tension.

In the embodiment depicted, the reference water level with respect to which the position of the tube 102 in the bath is regulated, is defined by filling the bath 101 to the very top. In order constantly to maintain the reference level and permanently to renew the coagulation liquid in the bath 101, the bath 101 is placed in an overflow tank 103 which has an overflow orifice 104. The coagulation bath 10 is connected by a pipe 12 to a source 13 of coagulation liquid which, during operation, continuously feeds the coagulation bath 101.

A second coagulation bath 14 is arranged vertically in line with the tube 102 to receive the fibre 11 and complete coagulation. The distance between the bottom end of the tube 102 and the level of liquid in the second coagulation bath 14 is set according to the desired tension on the fibre as it leaves the tube 102. The greater this distance, the greater the tension, which is caused by gravity. Incidentally, the second coagulation bath 14 is used to collect the liquid from the overflow tank 103 of the first coagulation bath 101. The second coagulation bath 14 is itself also connected to the source 13 of coagulation liquid and is equipped with an overflow pipe 15 allowing its contents to be continuously renewed.

The device comprises guide members 16, 17 for guiding the fibre out of the second coagulation bath 14 towards a rotary cylinder 18 intended for the temporary storage of the coagulated fibre. The cylinder 18 is arranged in a washing bath 19.

The temperature of the coagulation liquid in the baths 101 and 14, just like the temperature of the washing liquid in the bath 19 may be set to any datum value by virtue of temperature-regulating means (not depicted).

Figure 3:
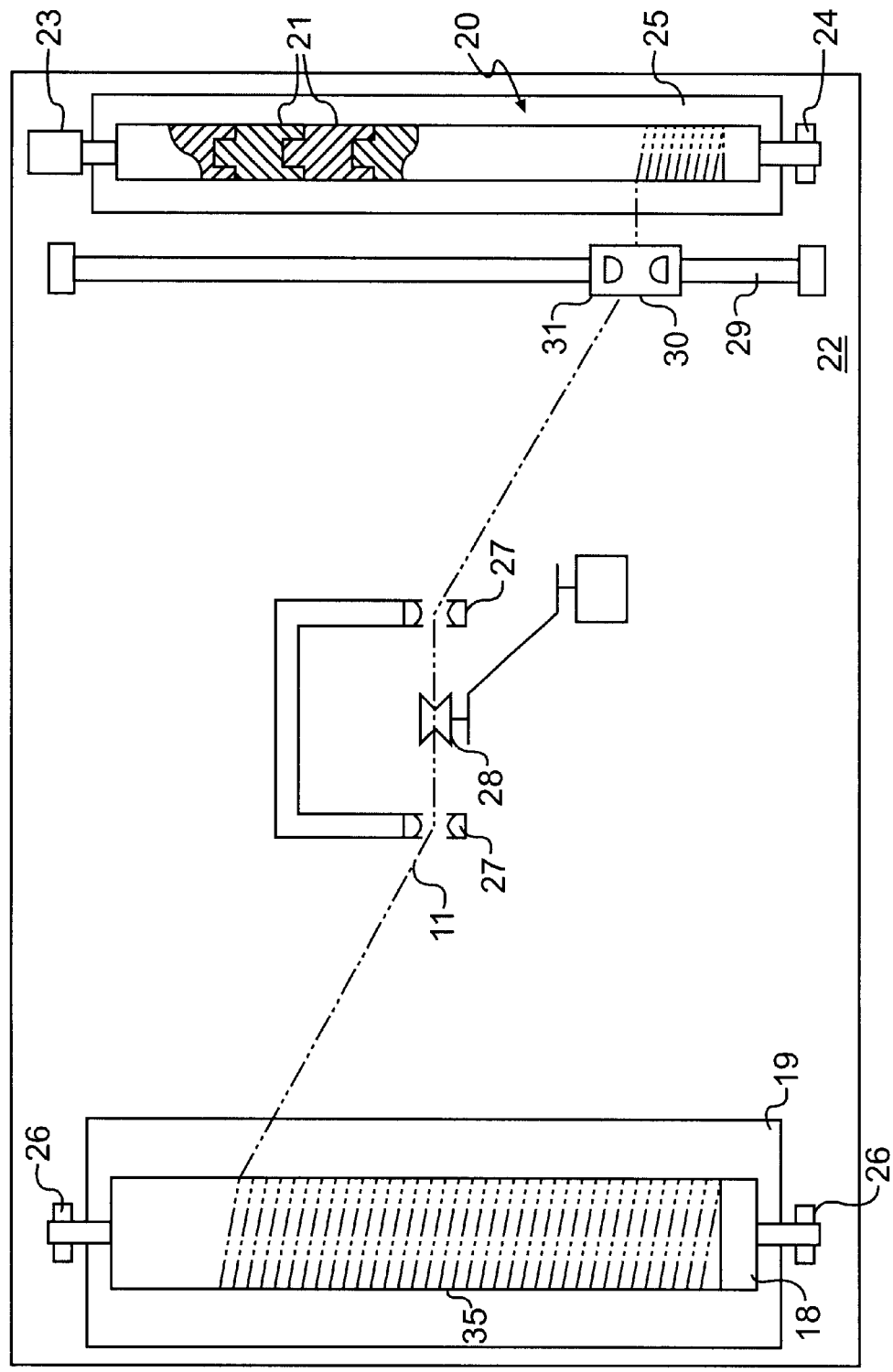
FIG. 3 depicts, diagrammatically, a view from above of a second part of a device for the manufacture of a segmented tubular capsule according to the invention.

In accordance with the invention, the device also comprises means of shaping the segmented tubular fibre. It has been seen that with certain polymer solutions if, during a determined period of time after the fibre has been removed from the coagulation bath, the fibre is subjected to mechanical deformation over a given time and at a given temperature, this deformation becomes permanent. In the embodiment depicted in FIG. 3, the shaping means comprise a cylindrical mandrel 20 consisting of portions 21 that fit together. This mandrel is mounted removably on a stand 22 so that it can be partially immersed in a second washing bath 25. One of its ends is coupled to a rotating motor 23 and its other end is supported by a bearing 24 and is free to rotate. The stand 22 further comprises support means (bearings 26) to receive the storage cylinder 18, so that the latter can rotate about its longitudinal axis and be arranged parallel to the mandrel 20. Between the storage cylinder 18 and the mandrel 20, there are various mechanical components secured to the stand 22 to allow part of the fibre wound on the cylinder 18 to be transferred onto the mandrel 20. These mechanical components comprise:—two guides 26, 27 allowing the fibre 11 to be kept perpendicular to the cylinder 18 and to the mandrel 20 over part of its length;—a tensioner 28 exerting a vertical thrust on the fibre 11 between the two guides 26, 27; —a guiding device comprising a rail 29 parallel to the mandrel 20 and a carriage 30 that can move along the rail 29 in a back and forth movement. The moving carriage is equipped with a guide 31 for the fibre 11.

The device just described operates as follows. The entire device is placed in a laminar-flow hood and all the liquids used (coagulation liquid, washing liquid) are sterile. The content of the coagulation baths 101, 14 and washing bath 19 are kept at constant temperature. The reservoirs 1, 2 are filled, one of them with polymer solution, and the other with a suspension of cells to be encapsulated. The temperature-regulating chamber is regulated to keep the suspension of cells at an appropriate temperature. The various baths 101, 14, 19 are filled. The value of the gas pressure for each of the reservoirs 1, 2 is communicated to the control unit 6. It is these values which, in particular, determine the rate at which the tubular fibre 11 flows out of the die 7. When the device has been started up, the control unit 6 controls the gas-pressure regulating system 5 in such a way that the supply of suspension of cells to the die 7 is interrupted at regular moments in time. The fibre which leaves the die is therefore a solid rod 11a, consisting only of polymer solution. According to the invention, to prevent the fibre 11 from breaking at this solid rod 11a, which is a drop of liquid, early solidification of the fibre is brought about by immersing it, a short distance from its exit from the die 7, in a coagulation liquid while driving it vertically downwards using the immersed tube 102. It has been found that when there is no drive, the fibre, experiencing upthrust in the coagulation liquid, deforms longitudinally into zigzags and exhibits a very uneven cross section, which makes it unusable as an implant. As mentioned above, it is also possible to set the height of the tube 102 in the bath 101 in such a way as to create a tensile force on the fibre 11 that allows the dimensions of the fibre (outside diameter, wall thickness) to be regulated independently of the dimensions of the nozzles 71, 72 of the die 7. As soon as the fibre 11 enters the coagulation liquid, solvent/nonsolvent exchange (which defines coagulation) occurs from the outside of the fibre and limits the undesirable effects of purely internal coagulation which begins as soon as the suspension of cells comes into contact with the polymer solution. In other words, the amount of solvent (which is somewhat toxic to the cells) which is extracted from the fibre from the outside represents so much less solvent liable to migrate into the suspension of cells during the process of coagulation from the inside.

The fibre 11 which emerges from the tube 102 is received in the second coagulation bath 14 where it solidifies enough that it can be handled. Note that the coagulation liquid in the baths 101 and 14 is permanently renewed in order to eliminate the solvent. The fibre is then washed and wound onto the storage cylinder 18 to form a single spiral starting and finishing respectively at each end of the cylinder.

To shape the fibre, a mandrel 20 is mounted on the rig 22. One end of the fibre wound onto the cylinder 18 is passed through the guides 26, 27 and then into the guide 31 of the carriage 30 of the guiding device and is attached to one end of the mandrel 20. The length of the disassemble portions 21 of the mandrel 20, just like their diameter, are designed for the definitive storage and shaping of implantable capsules comprising a determined number of compartments 11b. The speed of the motor 23 that rotates the mandrel 20, and the linear speed of the carriage 30 of the guiding device are chosen to be such that a section of fibre comprising a whole number of compartments 11b is wound onto each portion 21 of the mandrel 20, and that there is a section of fibre formed of solid rod 11a at each end of each mandrel portion 21. The rotational speed of the mandrel 20 is increased each time the fibre reaches the end of each mandrel portion 21 so that the formed turns of solid rod are further apart than the rest of the turns and so that separating two adjacent implantable capsules is easier. A single spiral is formed on the mandrel 20, starting and ending respectively at each end of the mandrel. The implantable capsules can then be separated from one another while at the same time keeping them, for storage and transport, attached to the mandrel portion on which they have been respectively spiral-wound.

Example 1

The reservoir 2 was filled with a polymer solution containing 8% by weight of an acrylonitrile-sodium methallyl-sulphonate copolymer (known by the trade name AN69), 6% by weight of physiological saline (solution of sodium chloride in water, at a concentration of 9 g/l) and 86% of dimethyl sulphoxide (DMSO). The contents of the reservoir were at ambient temperature (about 25° C.).

The reservoir 1 was filled with a suspension of islets of Langerhans at a concentration of 10 000 EI/ml (EI= equivalent islet, corresponding to a theoretical islet 150 µm in diameter) in agarose (Sigma Type IA—A 0169—batch No.—54 H 0530) at 0.5% (weight/volume) resulting from mixing a suspension of islets in HAM'S F12 (Sigma N8641—batch No.—123 H 2322) and a 0.65% (weight/volume) solution of agarose in physiological saline. The contents of the reservoir 1 were kept at 40.5° C.

The coagulation baths 101 and 14 are filled with sterile physiological liquid which is permanently renewed. The die used, manufactured by the company SCP-France had the following dimensions: inside diameter of the outer nozzle 72=1570 µm; outside diameter of the inner nozzle 71=980 µm; inside diameter of the inner nozzle 71=860 µm.

The tube 102 of the means for bringing about early solidification of the fibre 11 was a glass tube with an inside diameter of 0.003 m and a length of 0.25 m. The position of the tube 102 with respect to the coagulation bath 101 was adjusted such that the height of water between the top end of the tube 102 and the reference level was 0.005 m. The bottom end of the tube 102 was placed 0.05 m from the level of liquid in the second coagulation bath 14.

The height of the die 7 above the coagulation bath 101 was regulated such that the orifice of the die 7 was 0.002 m from the reference water level.

The contents of the coagulation baths 101, 14 and washing bath 19 were maintained at 25° C.

The datum values for the operating parameters communicated to the control unit 6 were as follows: pressure in reservoir 1=atmospheric pressure +80 mmHg; pressure in reservoir 2=atmospheric pressure +100 mmHg; the time for which the injection of the suspension of cells through the die 7 was interrupted was set at 0.40 seconds every 5.8 seconds.

Under these operating conditions, and with the hardware described above, there was obtained, after the start-up phase, a segmented tubular fibre with an inside diameter of about 1050 µm, a wall about 150 µm thick, and internal compartments about 0.6 m long. An implantable capsule containing about 30 000 EI, formed with this tubular fibre, was about 3.2 m long (namely five compartments).

The fibre 11 was transferred from the cylinder 18 onto the mandrel 20 one hour after the fibre was manufactured. After 18 hours at 37° C., the fibre detached from the mandrel 20 retained a spiral shape.

Example 2

Reservoir 2 was filled with a polymer solution containing 16% by weight of an acrylonitrile-vinyl acetate copolymer and 84% by weight of dimethylformamide (DMF). The contents of the reservoir 2 were at ambient temperature (about 25° C.).

The reservoir 1 was filled with a solution of Blue Dextran (Sigma—D5751) at a concentration of 1% by weight in physiological saline. The contents of the reservoir 1 were at ambient temperature.

The coagulation baths 101 and 14 were filled with sterile physiological liquid which was permanently renewed. The die used was the same as the one used in Example 1.

The tube 102 of the means for bringing about solidification of the fibre 11 was a glass tube with an inside diameter of 0.003 m and a length of 0.10 m. The position of the tube 102 with respect to the coagulation bath 101 was adjusted such that the height of water between the top end of the tube 102 and the reference level was 0.005 m. The bottom end of the tube 102 was placed 0.05 m from the level of liquid in the second coagulation bath 14.

The height of the die 7 above the coagulation bath 101 was regulated such that the orifice of the die 7 was 0.002 m from the reference water level.

The contents of the coagulation baths 101, 14 and washing bath 19 were maintained at 25° C.

The datum values for the operating parameters communicated to the control unit 6 were as follows: pressure in reservoir 1=atmospheric pressure +39 mmHg; pressure in reservoir 2=atmospheric pressure +360 mmHg; the time for which the injection of the solution of Blue Dextran through the die 7 was interrupted was set at 0.75 seconds every second.

Under these operating conditions, and with the hardware described above, there was obtained, after the start-up phase, a segmented tubular fibre with an inside diameter of about 980 µm, a wall about 180 µm thick, and internal compartments about 0.05 m long.

The fibre 11 was transferred from the cylinder 18 onto the mandrel 20 one hour after the fibre was manufactured. After 24 hours at ambient temperature, the fibre detached from the mandrel 20 retained a spiral shape.

Example 3

The reservoir 2 was filled with a polymer solution containing 15% by weight of polyethersulphone (PES), 5% by weight of polyethylene oxide with a molecular mass=10 kdaltons (Sigma—P6667), and 80% by weight of N-methylpyrrolidone (NMP). The contents of the reservoir 2 were at ambient temperature (about 25° C.).

The reservoir 1 was filled with a solution of Blue Dextran (Sigma—D5751) at a concentration of 1% by weight in physiological saline. The contents of the reservoir were at ambient temperature.

The coagulation baths 101 and 14 were filled with sterile physiological liquid which was permanently renewed. The die used was identical to the one used in Example 1.

The tube 102 of the means for bringing about solidification of the fibre 11 was a glass tube with an inside diameter of 0.003 m and a length of 0.10 m. The position of the tube 102 with respect to the coagulation bath 101 was adjusted such that the height of water between the top end of the tube 102 and the reference level was 0.005 m. The bottom end of the tube 102 was placed 0.05 m from the level of liquid in the second coagulation bath 14.

The height of the die 7 above the coagulation bath 101 was regulated such that the orifice of the die 7 was 0.002 m from the reference water level.

The contents of the coagulation baths 101, 14 and washing bath 19 were maintained at 25° C.

The datum values for the operating parameters communicated to the control unit 6 were as follows: pressure in reservoir 1=atmospheric pressure+50 mmHg; pressure in reservoir 2=atmospheric pressure+110 mmHg; the time for which the injection of the solution of Blue Dextran through the die 7 was interrupted was set, during a first test, at 0.35 seconds every 1.25 seconds, then during a second test at 0.32 seconds every 0.55 seconds.

Under these operating conditions, and with the hardware described above, there was obtained, after the start-up phase, a segmented tubular fibre with an inside diameter of about 900 $\mu$m, a wall about 100 $\mu$m thick, and internal compartments about 0.08 m long during the first test, and 0.03 m long during the second test.

The fibre 11 was transferred from the cylinder 18 onto the mandrel 20 one hour after the fibre was manufactured. After 24 hours at ambient temperature, the fibre detached from the mandrel 20 retained a spiral shape.

The invention is not restricted to the embodiment just described and can be varied.

What is claimed is:

1. Device for manufacturing a tubular fibre comprising a wall delimiting internal compartments isolated from one another and containing a biologically active medium, the device comprising:

extrusion means for coextruding a solution of at least one polymer and the biologically active medium to cause formation of a tubular fibre having a wall made from the polymer solution and containing the biologically active medium;

means for supplying the extrusion means with the polymer solution and with the biologically active medium;

means for controlling simultaneous supply of polymer solution and biologically active medium to the extrusion means and for interrupting the supply of biologically active medium at time intervals so as to form within the fibre successive compartments containing the biologically active medium and separated by a partition section formed from the polymer solution; and means for causing partial solidification of the fibre as it leaves the extrusion means, the partial solidification being sufficient to prevent the fibre from breaking at the partition sections.

2. Device according to claim 1, wherein the means for causing partial solidification of the fibre comprises:

a bath located adjacent the extrusion means, the bath for containing a coagulation liquid and being positioned to cause an exterior portion of fiber exiting the extrusion means to at least partially solidify upon exiting the extrusion means; and drawing means for causing the fibre to move through the coagulation liquid.

3. Device according to claim 1, further comprising tension exerting means for exerting a tensile force on the fibre so as to provide the fibre with at least one geometric characteristic independent of dimensions of the extrusion means.

4. Device according to claim 3, wherein the drawing means and the means for exerting a tensile force comprise a tube passing through a bottom of the coagulation bath and having an upper end inside the bath and a lower end outside the bath, the tube being arranged substantially vertically with the upper end lying below a surface of the coagulation liquid when the bath is filled to a reference level.

5. Device according to claim 2 further comprising liquid renewing means for continuously renewing the coagulation liquid.

6. Device according to claim 1, further comprising a washing bath for washing the fibre.

7. Device according to one of claims 2 or 5, further comprising means for regulating the temperature of at least one of the coagulation liquid and the washing liquid.

8. Device according to claim 1 further comprising means for shaping the fibre.

9. Device according to claim 8, wherein the means for shaping the fibre is configured to shape the fibre in a spiral and further comprises:

a mandrel;

means for rotating the mandrel; and a guiding device for moving the fibre with a reciprocating movement substantially parallel to the mandrel.

10. Device according to claim 9, wherein the mandrel is made of disassemblable portions.

11. Device according to claim 9, wherein in operation, a rotational speed of the mandrel and a speed of reciprocating movement of the guiding device are chosen so that a portion of fibre wound in a spiral onto the mandrel corresponds approximately to a whole number of internal compartments of the fibre.

12. Device for manufacturing a tubular fibre comprising a wall delimiting internal compartments isolated from one another and containing biologically active medium, the device comprising:

an extrusion head having an inner nozzle and a substantially concentric outer nozzle, the head for coextruding a solution of at least one polymer and the biologically active medium in a manner forming a tubular fibre having a wall made from the polymer solution and containing the biologically active medium;

a first reservoir flow connected to the inner nozzle for containing the biologically active medium;

a second reservoir flow connected to the outer nozzle for containing the polymer solution;

a flow regulating system for causing the biologically active medium and the polymer solution to flow from the first and second reservoirs to the extrusion head;

a control unit for controlling the flow regulating system so as to simultaneously supply the extrusion head with polymer solution and with biologically active medium and to interrupt the supply of biologically active medium at time intervals so as to form within the fibre successive compartments containing the biologically active medium and separated by a partition section formed from the polymer solution; and a bath for a coagulation liquid, the bath being located adjacent the extrusion head and being positioned to cause at least partial solidification of the fibre as the fibre leaves the extrusion head.

13. Device according to claim 12, wherein the flow regulating system comprises a gas pressure regulator for setting and maintaining a substantially constant pressure in each of the first and second reservoirs.

14. Device according to claim 12, further comprising a tube passing through a bottom of the coagulation bath and having an upper end inside the bath and a lower end outside the bath, the tube being arranged substantially vertically with the upper end lying below a surface of the coagulation liquid when the bath is filled to a reference level.

* * * * *